United States Patent
Shoham (10) Patent No.: US 8,571,638 B2
(45) Date of Patent: Oct. 29, 2013

(54) MINIATURE BONE-ATTACHED SURGICAL ROBOT AND METHOD OF USE THEREOF

(75) Inventor: Moshe Shoham, Hoshaya (IL)

(73) Assignee: Mazor Robotics Ltd., Caesarea (IL)

( * ) Notice: Subject to any disclaimer, the term of this patent is extended or adjusted under 35 U.S.C. 154(b) by 33 days.

(21) Appl. No.: 12/725,481

(22) Filed: Mar. 17, 2010

(65) Prior Publication Data
US 2010/0198230 A1 Aug. 5, 2010

Related U.S. Application Data

(63) Continuation of application No. 10/965,100, filed on Oct. 15, 2004, now abandoned, which is a continuation of application No. 09/912,687, filed on Jul. 24, 2001, now Pat. No. 6,837,892.

(60) Provisional application No. 60/220,155, filed on Jul. 24, 2000.

(51) Int. Cl.
*A61B 19/00* (2006.01)

(52) U.S. Cl.
USPC ............ 600/427; 600/407; 600/410; 606/130

(58) Field of Classification Search
USPC ................... 600/417, 421, 427, 429; 606/130
See application file for complete search history.

(56) References Cited

U.S. PATENT DOCUMENTS

| 5,690,106 A | * | 11/1997 | Bani-Hashemi et al. ...... 600/425 |
| 5,951,475 A | * | 9/1999 | Gueziec et al. ............... 600/425 |
| 6,529,765 B1 | * | 3/2003 | Franck et al. .................. 600/427 |

OTHER PUBLICATIONS

Article entitled, "The Application Accuracy of the NeuroMate Robot—A Quantitative Comparison with Frameless and Frame-Based Surgical Localization Systems," Qing Hang Li et al., Computer Aided Surgery vol. 7 No. 2, pp. 90-98 (2002), Wiley InterScience.

* cited by examiner

*Primary Examiner* — Tse Chen
*Assistant Examiner* — Mark Remaly
(74) *Attorney, Agent, or Firm* — Daniel Feigelson (57) ABSTRACT

A miniature surgical robot is attached directly to the bone of a patient at a surgical site, thereby locating the robot precisely on the bone. Intraoperative two-dimensional images of the robot on the bone together with an image referencing element disposed in a predetermined position relative to the robot, are correlated to form a three dimensional image. One or more windows of this three dimensional image are registered with similarly located windows in a preoperative three-dimensional image of the surgical site, the preoperative image including details of the surgeon's plan. This registration of these windows defines the referencing element position in the preoperative image, and hence the robot location in the preoperative image. This enables the robot to be directed to pre-operative determined positions based on the pre-operative plan to perform a surgical procedure.

30 Claims, 5 Drawing Sheets

MINIATURE BONE-ATTACHED SURGICAL ROBOT AND METHOD OF USE THEREOF

This Application is a continuation of application Ser. No. 10/965,100, filed Oct. 15, 2004 now abandoned, which is a continuation of application Ser. No. 09/912,687, filed Jul. 24, 2001, now U.S. Pat. No. 6,837,892, which claims priority from Provisional Application Ser. No. 60/220,155, filed Jul. 24, 2000. The contents of all of the above-listed applications are incorporated herein by reference.

TECHNICAL FIELD

The present invention relates to a robotic device. Particularly, this invention relates to a robotic device that attaches to a bone of the patient and aids or performs surgical procedures.

BACKGROUND OF THE INVENTION

Generally, robots are used in many different industries for many different applications. One industry, for example, is the medical industry that uses robots in applications including assisting the surgeon during surgical procedures. Robots are especially suited for some surgical tasks because they can be constructed to be very steady, computer controlled, and precise in their movements. Characteristics such as these can be especially helpful during surgery on sensitive areas, such as, for example, the vertebral column but are applicable throughout the body.

Typical vertebral column surgical procedures include vertebral fusion, insertion of medical devices such as pedicle screws, discography, percutaneous discectomy, or the like. These procedures typically require a large invasive operation that exposes the patient to a high risk of infection, excessive trauma, fluid loss, post operative pain, scarring, and a lengthy recovery time. Some difficulties relating to surgery on the vertebral column include micro-movement of the vertebral column during the operation, inherently small target objects of the procedure such as the pedicles, extremely delicate nearby nerve tissue, and limited operating room space because large equipment is needed to aid in the procedure, such as C-arm X-ray devices. Furthermore, the patient and operating room staff are exposed to large doses of radiation because these procedures require repeated X-raying and/or fluoroscoping of the surgical site so the surgeon can view the position of surgical tools or implants relative to non-visible body parts.

A need exists for a device that can assist minimally invasive surgery with low radiation exposure while allowing the surgeon to precisely align and control or monitor the surgical procedure. Some prior art devices have attempted to accomplish this however, these devices are either too complicated, not sufficiently accurate, or consume too much operating room space.

One such device is disclosed in U.S. Pat. No. 6,226,548. This device combines a navigation system, a bone mounted apparatus, and surgical tools that communicate with the navigation system. This apparatus primarily consists of a clamp that attaches to the patient's spine and extends outward forming a reference arc bearing emitters or a tracking means. All the surgical tools used in this procedure are fitted with emitters or a tracking means similar to the reference arc. The surgical suite is fitted with a navigation system capable of recognizing the emitters or tracking means of the reference arc and surgical tools, a computer system for interpreting the location of the tools, and a video display for the surgeon. After surgically placing the clamp and reference arc on the patient a CT or MRI is taken creating a three-dimensional image of the patient with the attached device. When the patient is in place in the surgical suite with the attached reference arc the navigation system locates the arc and the surgical tools and displays them, relative to each other, on the three-dimensional CT scan.

While the device disclosed in the '548 patent offers some advantages in terms of accuracy and reduced trauma, the advantages of this type of prior art device are limited. The critical part of a surgical tool that must be monitored is the working end of the tool, whether that be a screwdriver or a drill bit or the like. These cannot be tracked with such prior art systems. Transmitters or emitters cannot be attached to the working ends of tools so the computer must estimate the location of the working end by locating the tool generally and extrapolating. This causes inaccuracy and errors that cannot be tolerated in spinal surgery or other high accuracy procedures where the smallest error can result in a serious and permanent outcome. Also, prior art devices such as these are hand held by the surgeon and thus, limited in accuracy to the surgeon's ability to hold and align the tool.

Furthermore, when using this system, the user must be cautious to not block the line-or-sight between the tool mounted emitters or receivers, the reference arc bearing emitters or receivers, and the navigation system. This can severely limit the ability of the surgeon or surgical team as the tool may actually limit their ability to aid the patient. Also, while such prior art systems do reduce the incision size, they complicate the surgical procedure. Usually a patient is brought into a surgical suite ready for a procedure, the procedure is performed, completed, and the patient leaves. However, the '548 patent system requires the patient to be put through a surgical procedure to affix the clamp and referencing arc, then the patient is transported to a CT or MRI, then transported back to the surgical suite in a non-sterile condition for the substantial portion of the procedure to commence. Finally, this system has many components, such as the navigation system and the computer output unit, that clutter up the already limited space in the surgical suite.

Therefore, there is a need in the art for a device with high precision and accuracy that can assist the surgeon in aligning the working end of the surgical tool such that delicate procedures can be preformed percutaneously with minimal radiation exposure to both the patient and the surgical staff.

SUMMARY OF THE INVENTION

The present invention is directed to a device and method for assisting in surgical procedures. According to the invention, a robot is disclosed that precisely positions a surgical tool with respect to a surgical site. The robot attaches to the bone of a patient with a clamp or with wires such as K-wires. Actuators extend from the robot base and move away from and toward the base member. This manipulates balls that rotate within spherical swivel joints that in turn align a sleeve. A surgical tool such as a screw driver or a drill bit is inserted through the sleeve and thus is precisely aligned with a site requiring surgery.

The present invention also includes a method for using the robot to assist in surgical procedures. Initially, three dimensional images are taken of the patient and the surgeon performs pre-operative planning of the procedure to be done on the images. This creates parameters that will later be used to direct the robot to the location where the surgical procedure is required. The robot is then attached to the patient by the clamp or the k-wire. C-arm images are taken of the patient with the attached clamp and these images are co-registered and calibrated such that a precise image of the bone with the robot attached is generated. This image is then registered, or matched, with the three dimensional image. This is accomplished in a highly efficient and accurate manner by taking small windows of the images where the surgery is to take place and registering these small portions. The small windows are chosen off the images by locating the bone attached clamp and selecting a window according to pre-operative calculation of the bone-robot attachment location. After these windows are chosen and registered, the remaining bone is registered by aligning the registered windows. At this point the robot is located precisely on the bone of the patient in the three dimensional image and can be manipulated by the surgeon to a pre-operative planned location for percutaneous insertion of surgical tools, medical devices, or implants.

BRIEF DESCRIPTION OF THE DRAWINGS

For a better understanding of the nature, objects, and function of the present invention, reference should be made to the following detailed description in conjunction with the accompanying drawings, in which.

Like reference numerals refer to corresponding elements throughout the several drawings.

DETAILED DESCRIPTION OF THE PREFERRED EMBODIMENT

Figure 1:
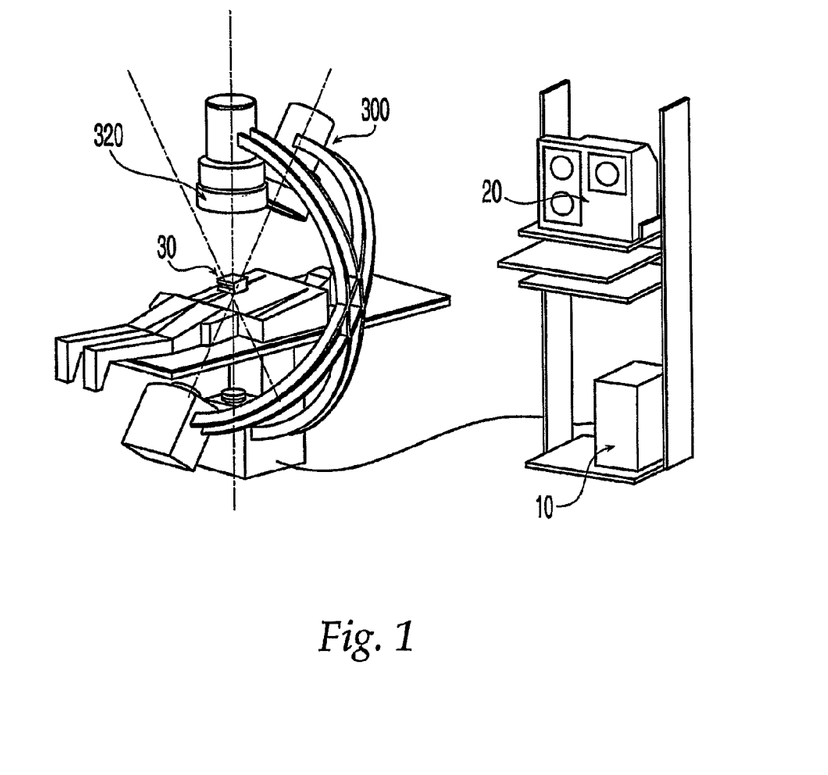
FIG. 1 is an overview of an embodiment of a surgical system showing a control unit with a display, C-arm with a calibration phantom attached, and a robot used for aligning surgical tools attached to the patient according to the present invention.

Referring to the illustrations and particularly to FIG. 1 it can be seen that a preferred embodiment of the present invention generally includes an image guided, robot assisted, surgical system. Included in this system generally, as shown in FIG. 1, is a bone attached surgical robot 30; a control unit 10 that matches data from CT scans and C-arm images to locate robot 30 on the patient's bone and allows a surgeon to control robot 30, through the use of a mouse, joystick, touch screen, or the like; and video display 20. Control unit 10 generally includes a cpu and user interface communicating with display 20 and robot 30.

Figure 2:
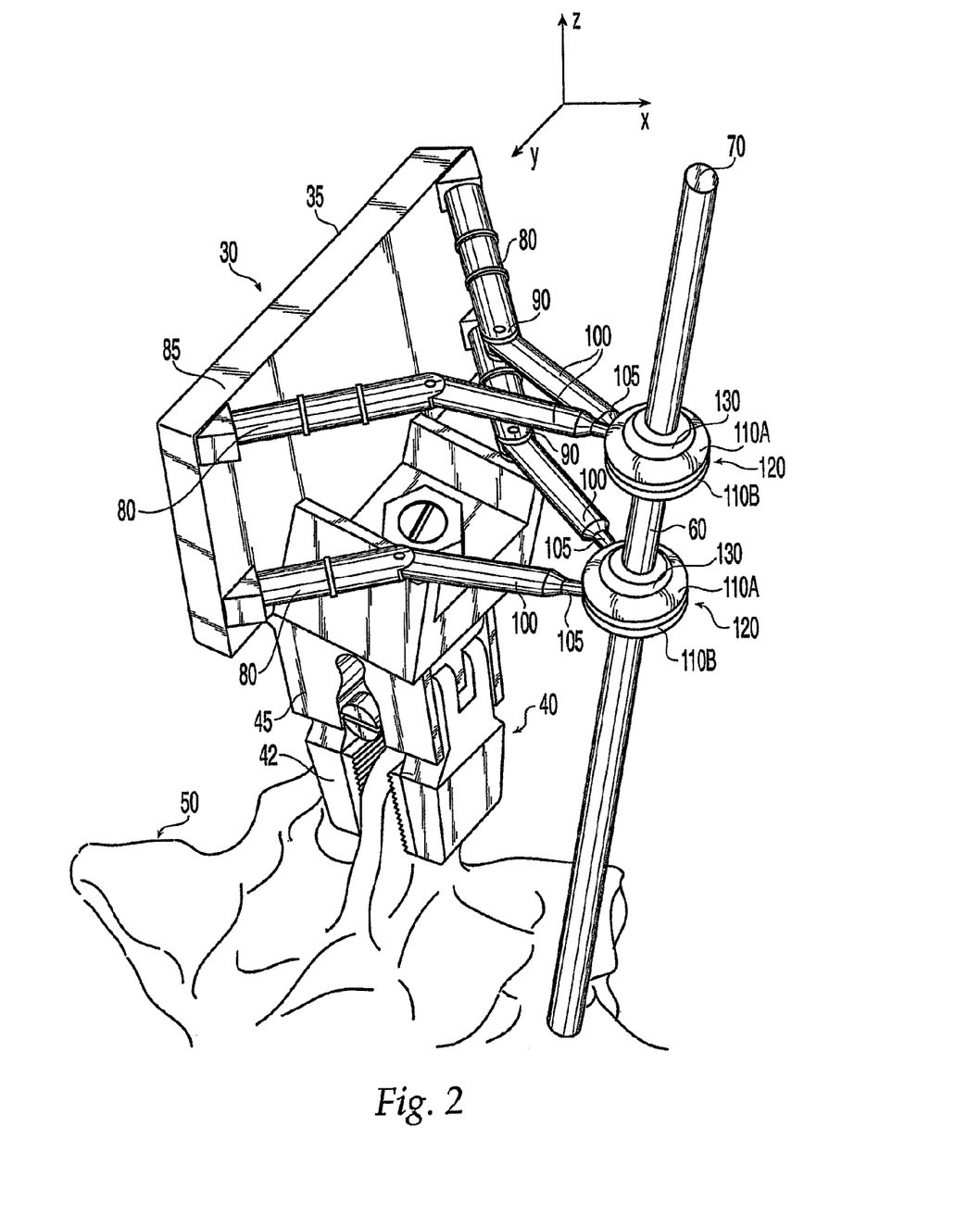
FIG. 2 is a perspective view showing a miniature surgical robot attached to a bone and aligning a surgical tool in an embodiment of the invention.

FIG. 2 illustrates robot 30 according to one embodiment of the present invention attached with clamp 40 to vertebra 50. Robot 30 aligns sleeve 60 through which surgical tool 70 such as a screwdriver, drill bit, Kirschner wire (K-wire), or the like can be inserted and precisely aligned with a site requiring a surgical procedure and thus, the operation can be conducted percutaneously or in traditional open procedures.

In a preferred embodiment of the invention, robot 30 includes base 35 that sits vertically on clamp adaptor 45. At least two pairs of actuators 80 extend from base 35. The actuators 80 extend from the base 35 forming a fixed angle 85 between base 35 and actuator 80. This angle is generally between about 15-90 degrees and more preferably about 45 degrees. In one preferred embodiment, the points of attachment of actuators 80 are spaced apart by about 50 mm in the Z direction and about 50 mm in the Y direction. Each actuator 80 is capable of operating independently from the other actuators 80. Actuator 80 is similar to known linear actuators and includes a housing, a motor, a lead screw, an electrical connection, and a position sensor such as an optical encoder, an LVDT, or the like. In a preferred embodiment each actuator is approximately 5 mm in diameter and approximately 35 mm in length.

The end of actuator 80 that is not fixedly attached to base 35 contains hinge joint 90. Hinge joint 90 links actuator 80 to rigid member 100. In a preferred embodiment member 100 is about 4 mm in diameter and 40 mm in length. Hinge joint 90 permits member 100 to freely rotate through about 270 degrees on an axis that runs parallel to base 35. The other end of the rigid member 100 is fixed with solid connection 105 to ring member 110. There is no movement between rigid member 100 and ring member 110 at solid connection 105.

Upper ring member 110A and lower ring member 110B, solidly connected to individual rigid members 100, come together at spherical swivel joint 120. Each ring member 110 forms one half of an outer race of spherical swivel joint 120. Ring members 110 are free to rotate with respect to one another, but are held fixedly from separating in the Z axis direction. Contained between upper ring member 110A and lower ring member 110B, and free to swivel, is ball 130. Passing through ball 130 is sleeve 60. Sleeve 60 passes through both upper and lower balls 130, forming an aligning axis through which surgical tool 70 is passed. As actuators 80 extend and retract, hinge joints 90 freely rotate about the Z axis and balls 130 swivel in the spherical swivel joints 120 formed by upper and lower ring members 110. A hollow axis is formed by the sleeve passing through each of upper and lower balls 130 such that a surgical tool 70 can be inserted through and be accurately aligned with the working location.

According to the present invention the above described robot 30 is just one example of a robot configured for surgical assistance that may be utilized with the system according to the present invention. Other robot configurations that could satisfy the same tasks include, for example, a parallel robot constructed to the required dimensions, such as that described in Simaan, N., Glozman, D., and Shoham, M.: "Design Considerations of new types of Six-Degrees-of-Freedom Parallel Manipulators," IEEE International Conference on Robotics and Automation, Belgium, 1998, which is incorporated by reference herein.

Figure 3:
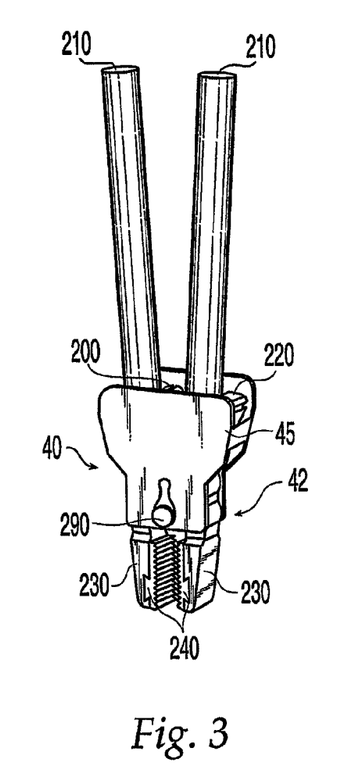
FIG. 3 is a perspective view showing a clamp for attaching to a bone and adaptor for receiving a robot in an embodiment of the invention.
Figure 4:
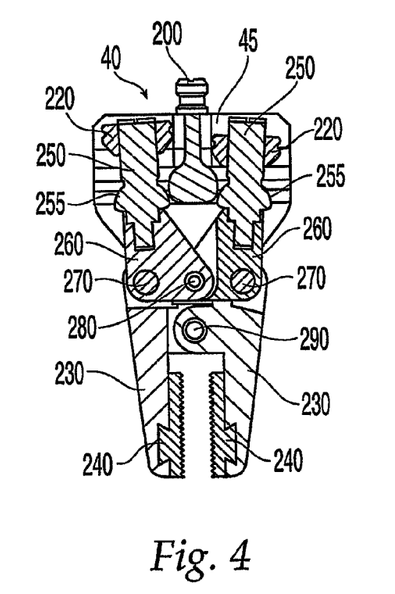
FIG. 4 is a cross-sectional view of FIG. 3.

In a preferred embodiment of the invention, robot 30 is attached with the bone of a patient by clamp 40. As shown in FIGS. 3 and 4, clamp 40 comprises bone clamping portion 42 and clamp adaptor 45. Initially, handles 210 extend from clamp 40 and allow a user to hold, align, and affix clamp 40 onto a bone of the patient. The base of the handles 210 fit over nuts 220, shown in FIG. 4, located on clamp 40. When clamp 40 is in place, the user pushes handles 210 toward each other to close jaws 230 onto the selected bone. When handles 210 are fully closed, or pushed together, a first locking (described below) occurs and clamp 40 is locked in place on the bone. The user then rotates handles 210 in a clockwise direction, turning and tightening nuts 220. Nuts 220 tighten down on threaded studs 250 and pinch clamp adaptor 45 onto bone clamping portion 42. This causes a second locking of clamp 40 into place on the bone. The base of each threaded stud 250 has a spherical mating surface 255 so that when clamp adaptor 45 is tightened down onto bone clamping portion 42 the clamp adaptor can self align itself on spherical mating surface 255 of stud 250. This allows the top surface of clamp adaptor 45 to maintain a horizontal surface for receiving the robot base 35. The handles, 210, are then removed by pulling straight up and away from the clamp 40. Protruding from the top surface of clamp adaptor 45 are connection pins 200. Connection pins 200 align with receiving holes in robot base 35 and when inserted lock robot 30 into place by some type of a snap ring or spring and ball bearing or plunger ball/pin.

With reference specifically to FIG. 4, it can be seen that threaded studs 250 are embedded in levers 260. Left and right levers 260 are connected together by upper center hinge 280. The other end of levers 260 connect with respective jaws 230 through side axis hinge 270. Left and right jaws 230 are connected together by main pivot 290 around which the jaws rotate. When a user pushes handles 210 together to close jaws 230, upper center hinge 280 is pushed downward and at the same time side axis hinges 270 rotate around the main pivot 290. The first locking occurs when upper center hinge 280 is pushed below the center line formed between left and right side axis hinges 270, and clamp 40 locks onto the bone. When clamp 40 is in the fully closed and locked position, jaws 230 are parallel to each other and separated by a set distance. The set closing distance between jaws 230 can be altered for different bone attachment applications by exchanging re-moveable jaw inserts 240 with the same of a different thickness.

Figure 7:
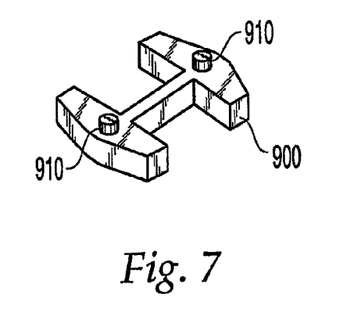
FIG. 7 is a perspective view of a spacer used to extend the clamp.

FIG. 7 illustrates spacer 900 that can be attached to the top surface of clamp adaptor 45 to ensure that robot 30 remains above the working area and out of any tissue that might occur when a patient has unusual body proportions. Spacer 900 attaches to connector pins 200 of clamp adaptor 45 and provides connector pins 910, similar to connector pins 200, for robot 30 attachment to the top surface of the spacer 900.

Figure 8:
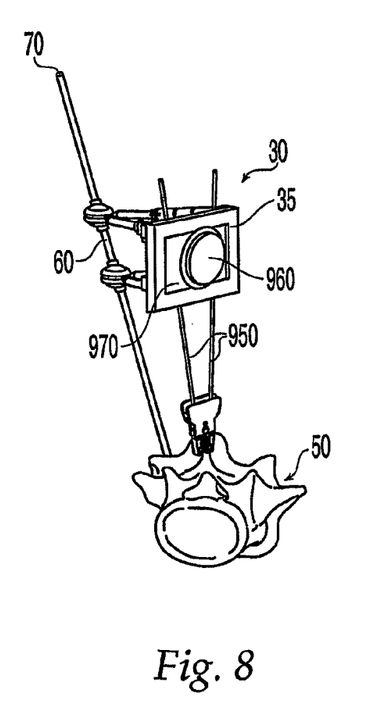
FIG. 8 is a perspective view showing a miniature surgical robot for aligning a surgical tool attached to a bone by K-wires in an embodiment of the invention.

Above described clamp 40 is an example of one embodiment according to the invention by which a robot may be attached to a bone for assisting in a surgical procedure. Other attachment devices can also be incorporated with a robot such as, for example, K-wire connections. FIG. 8 illustrates such a K-wire connection. K-wires 950 are inserted into the bone by standard surgical procedures. Robot base 35 contains an elongated slot through which K-wires 950 are inserted. Screw 960 can then be turned and tighten pinch plate 970 against robot base 35 pinching K-wires 950 between pinch plate 970 and robot base 35 holding robot 30 tight with respect to K-wires 950 and bone 50.

Figure 5:
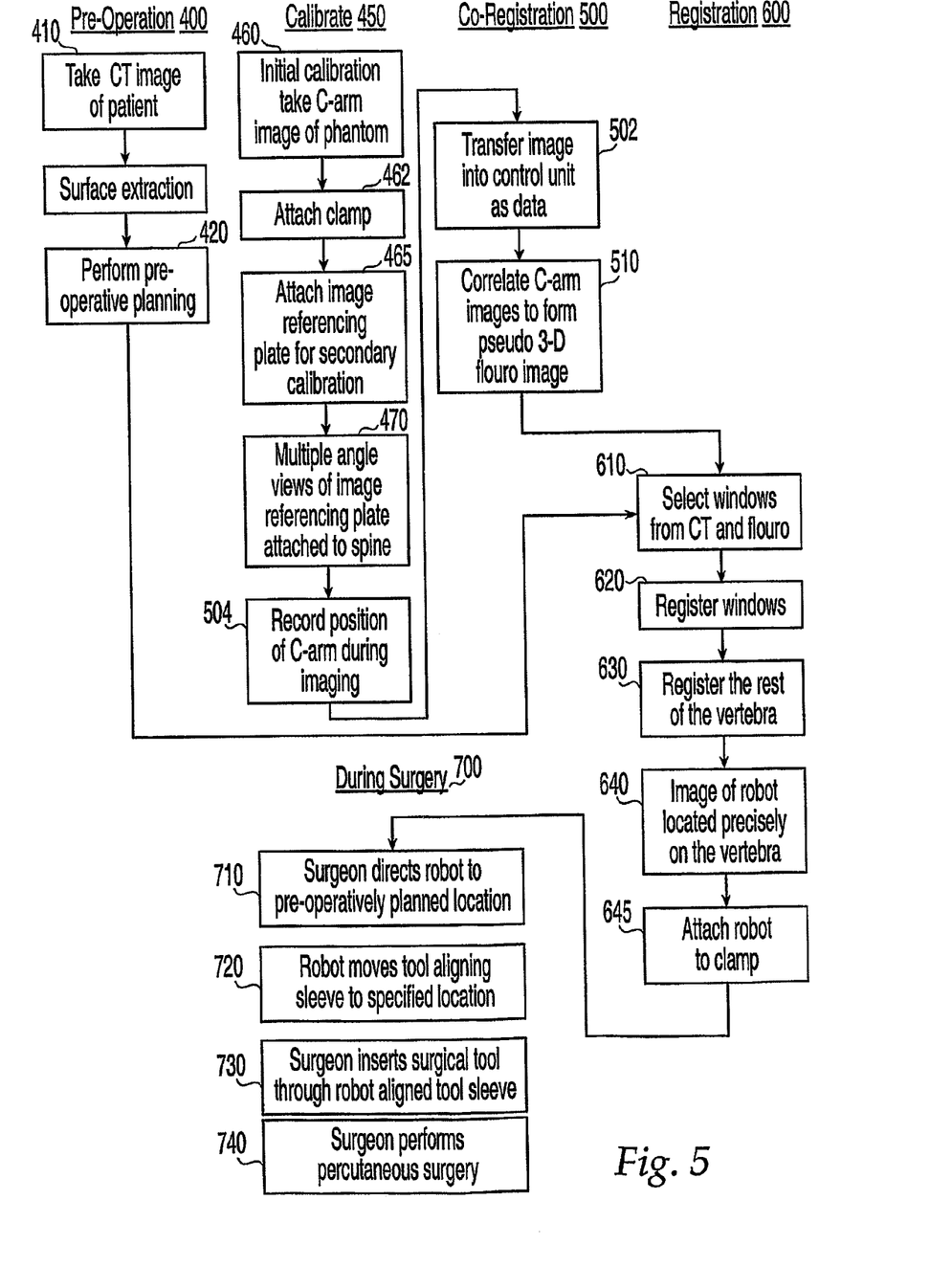
FIG. 5 is a flow chart of an embodiment of the method of using the present invention.

FIG. 5 illustrates the registration system used to establish the position of the robot on the bone. Initially there is a pre-operative step 400. This step 400 consists of taking a three-dimensional scan 410 of the patient, such as a CT or MRI scan. A surgeon then performs pre-operative planning 420 on the three-dimensional scan. For example, if the procedure to be done is a fracture fixation, the surgeon will study the three-dimensional image and the condition of the bone, choose the proper implant from a database containing implants of all types and sizes based on the present application, and electronically position and insert the implant, the screw, or the like. This is known in the art, for example, as described in "Marching Cubes: a high resolution 3D surface reconstruction algorithm", W. E. Lorensen, H. E. Cline, Computer Graphics 21 (1987) 163-169 which is incorporated by reference. The parameters generated by the pre-operative planning 420 are stored in the control unit 10 for positioning the robot 30 during the actual surgical procedure.

Figure 6:
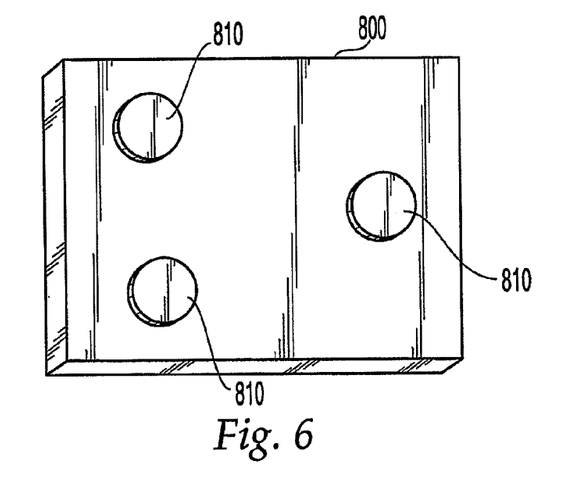
FIG. 6 is a perspective view of an image referencing plate with three referencing markers attached.

With reference now to FIGS. 1, 5, and 6 the next step is initial calibration of the C-arm 450. A phantom 320 (FIG. 1) is attached to the lens of the C-arm device 300 and a blank C-arm image is taken, step 460, FIG. 5. The phantom 320 is used to correct for the distortion associated with the C-arm image. The phantom contains several reference objects and a large number of small reference objects. The control unit automatically recognizes the reference objects and creates distortion correction maps and calibration intrinsic parameters to correct for the imprecise C-arm image. Systems such as these are known in the art and described, for example, in Brack et al., "Accurate X-ray Navigation in Computer-Assisted Surgery", Proc. Of the 12th Int. Symp On Computer Assisted Radiology and Surgery, H. Lemke, et al., eds., Springer, 1998; Yaniv et al., "Fluoroscopic Image Processing for Computer-Aided Orthopaedic Surgery", Proc. 1st Int. Conf. On Medical Computing and Computer-Assisted Intervention, Lecture Notes in Computer Science 1496, Elsevier, et al., eds., 1998; Hofstetteret al., "Fluoroscopy Based Surgical Navigation—Concept and Clinical Applications", Proc. 11th Int. Symp. on Computer Assisted Radiology and Surgery, H. U. Lemke, et al., eds., Springer 1997; Tsai, R., "A Versatile Camera Calibration Technique for High-Accuracy 3D Machine Vision Metrology Using Off-the-Shelf TV Cameras and Lenses", IEEE Journal of Robotics and Automation, Vol. RA-3, No. 4, August 1987, which are incorporated by reference.

Next, the patient is brought into the operating room, a small incision is made according to standard surgical practice at the site where clamp 40 is to be attached, and the clamp is attached to the selected bone using handles as described above, step 462, FIG. 5. Handles 210 are then removed from the clamp 40. An image referencing plate 800 (FIG. 6) is attached to clamp 40, step 465, FIG. 5, by receiving holes that receive connector pins 200. The image referencing plate 800 (FIG. 6) has three referencing markers 810 on it that show up very clear and precise in the C-arm image. The distance and angle between the referencing markers 810 are known such that the C-arm image can be calibrated in a secondary calibration step, step 465, to accurately represent actual size of the image. At least two, but preferably three C-arm images are taken of the patient with the attached clamp 40 and image referencing plate 800. These C-arm images are taken from different angles, preferably 0, 45, and 90 degrees, step 470, FIG. 5.

In another embodiment of the present invention the secondary calibration step, step 465B, can be accomplished by attaching the robot 30 to the clamp and taking multiple C-arm images. By knowing the dimensions, or by placing referencing markers on robot 30 and knowing the distance and angle between the referencing markers the C-arm images can be calibrated in a secondary calibration step, step 465B.

The next step of the process is co-registration, step 500. The C-arm images are transferred into the control unit 10 as data, step 502. At each location an image is taken from, the position of the C-arm is recorded, step 504, into the control unit 10. The data of the images, step 502, and the position of the C-arm, step 504, are correlated by knowing the position from which each images was taken, step 504, and by aligning the referencing markers 810 (FIG. 6) from the image referencing plate 800 (FIG. 6). Thus, an accurate, pseudo three-dimensional image of the surgical site with the clamp 40 attached to the bone is generated. This stage can be referred to as robot to bone registration or co-registration.

According to a preferred embodiment of the invention, bone to bone registration next occurs in step 600. Step 600 is a process of estimating and matching the true surface contours or the objects in the images. Registration methods are either based on geometry or intensity of the image. Geometric based registration is achieved by finding features in the 2D fluoroscopic images and matching these features with corresponding features in the 3D image, acquired, for example, from a CT scan dataset, MRI image, ultrasound image or from a CAD model. The features can be known landmarks (anatomical landmarks or implanted fiducials), or contour points in the fluoroscopic image, matched with the registered object's surface. An algorithm that may be used to compute the transformation is the Iterative Closest Point (ICP) algorithm. This algorithm is described, for example in Besl, P. J. and McKay, N. D., "A Method for Registration of 3D Shapes", IEEE Trans. on Pattern Analysis and Machine Intelligence, 1992, 14(2), 239-255, which is incorporated herein by reference. The input to the algorithm are sets of back-projected rays from the fluoroscopic images, and a model of the registered object. The algorithm iteratively computes a transformation that approximates the ray sets to the model. For landmark registration, a match between each ray and the corresponding landmark is defined before searching for the transformation. Contour registration selects a new surface point to match with each ray on every iteration.

Preferably, the registration process uses two or more fluoroscopic images, as described in greater detail, for example, in Hamadeh, et al., "Towards automatic registration between CT and X-ray images: cooperation between 3D/2D registration and 2D edge detection", Medical robotics and computer assisted surgery, 1995, Wiley 39-46, and Hamadeh, et al., "Automated 3-Dimensional Computed Tomographic and Fluoroscopic Image Registration", Computer Aided Surgery, 1998, 3, which are incorporated herein by reference. According to this method, anatomical landmarks in the images are detected and matched manually. Based on this match, an approximated initial guess is computed, with ray intersections, which are 3D points in the registration environment, being matched with the model's landmarks. Then, the object's contour in the 2D image is registered with the model's surface. A likelihood estimator is used to remove outliers, or pixels not in the contour, from the sample point set. A signed distance function is defined to overcome any internal contours problems. The overall in-vitro accuracy of this method can be better than 2 mm.

In one alternative, a single fluoroscopic image may be used for registration, achieving an accuracy of about 3 mm. This technique is based on a combinatorial search among matches of three points and three rays. The match with minimal average distance for the registration is then selected. This alternative is described in Tang, "Method for Intensity-based Registration with CT Images," Masters Thesis: Department of Computer Science, Queen University, Ontario Canada, 1999, which is incorporated herein by reference.

In a further alternative according to the invention, intensity-based registration is achieved by comparing fluoroscopic images with simulated X-rays (digitally reconstructed radiographs, or DRR's) from an estimated position. Such a technique is generally described in Lemieux et al., "Patient-to computed-tomography image registration method based digitally reconstructed radiographs", Medical Physics, 21, 1994, 1749-1760 and Murphy, M. "An automatic six-degree-of freedom image registration algorithm for image-guided frameless stereotactic surgery", Medical Physics, 24(6), June 1997, which are incorporated by reference herein.

When the camera position guess and the actual position are very close, the original and reconstructed image are very similar. Pixel intensity information is used to define a measure of similarity between the datasets. The similarity measure can include intensity values, cross-correlation, histogram correlation, and mutual information. The algorithm proceeds in three steps. The input is a CT data set, intrinsic camera parameters, one or more fluoroscopic images and an initial camera position estimate for each image. In the first step, the algorithm generates one DRR for each given camera position. In the second step, a dissimilarity measure is computed between the real and reconstructed image. In the third step, new camera poses are computed that best reduce the dissimilarity between the images. The process is repeated until convergence is reached. The parametric space of camera positions in then searched incrementally from an initial configuration. The space is six-dimensional (three rotations and three translations). The advantages of this technique is that no segmentation is necessary. However, the search space is six-dimensional, and can contain many local minima.

A benefit of the present invention is that it can utilize either of the above described registration methods. By utilizing the dimensions of the bone attached robot and its attachment location, the initial location of the window is a very good guess of the location and therefore the intensity based method can be utilized. Thus, according to the present invention, a faster and more accurate registration process is accomplished as between the fluorscopic and 3D images. This is done in step 600, and occurs very quickly and with a high degree of accuracy because the registration process is performed on small windows of the images, rather than the images as a whole. Preferably windows are selected that specifically relate to the known location of the robot and/or its support member. Windows of about 20 mm by 20 mm located approximately adjacent to the clamp location, according to pre-operative calculation of the bone-robot attachment location, are selected from the C-arm (fluoroscopic) image data, step 610. For example, these windows may be selected as the area above the attached clamp 40 in the C-arm image and the tip of the transverse process of the vertebra covering the area where the surgical procedure is to take place. Generally, the same windows are chosen from both the pseudo three-dimensional hybrid C-arm image, step 510, and also from the CT image (3D image), step 410. The small windows chosen from the C-arm images and the CT scan image are then laid over each other and matched or registered by the control unit, step 620, as described above. Focusing only on a small window of the C-arm image rather than looking for a matching anatomical landmark in the entire image, makes the process occur very fast and with the high degree of accuracy needed for precise procedures such as vertebra surgery.

Next, the remaining portion of the CT and C-arm image of the bones are overlaid, the registration windows are aligned, and the remaining bone is registered, step 630. Since the windows have already been accurately registered this step occurs quickly and also with a high degree of accuracy. Now clamp 40 is located precisely on the bone, step 640, of the CT image. Next, the user attaches robot 30 to clamp 40 and thus, robot 30 is located precisely with respect to the bone, step 645.

After robot 30 is co-registered 500 and registered 600, its position is known relative to the patient's bone and therefore can move to align with the pre-operatively picked location such that the operation can virtually take place on the control unit. The user selects a pre-operatively planned location and task from step 420 by use of a joystick, mouse, touch screen, or the like, step 710. The Robot 30 responds and moves sleeve 60 into position, step 720, such that when the user inserts a surgical tool 70 through the opening in the sleeve 60 the surgical tool 70 will be precisely aligned with the location requiring the surgical procedure, step 730. The surgeon can then insert a selected surgical tool 70 and operate without opening the surgical site to see the placement of the surgical tool because the surgeon can verify the positioning of the surgical tool 70 on the control unit 10 and display 20. Thus operating percutaneously or in general open procedures, with a high degree of accuracy, low trauma, small incisions, low chance of infection, and minimal exposure to radiation. A further benefit of this system is that because the robot is miniature it can be freely attached to the bone of a patient and move with the body. Therefore, the robot system does not need a dynamic referencing device to maintain orientation with the body once it is registered. This creates a more precise and less complicated system that is versatile and user friendly as the surgeon can manipulate the patient into different surgical positions without disturbing the robot system.

The present invention is illustrated herein by reference to a spinal vertebra attachment. However, it will be appreciated by those in the art that the teachings of the present invention are equally applicable to other bone attachments.

What is claimed is:

1. A method for performing a surgical procedure at a surgical site, comprising:
   utilizing an initial three dimensional image of said surgical site to provide a surgical plan of said procedure;
   attaching an attachment member to a bone associated with the surgical site, the attachment member being configured and dimensioned for use by a surgical robot;
   generating at least two intraoperative images of said surgical site including an image referencing element attached to said attachment member, such that the position of the attachment member is known relative to said image referencing element;
   thereafter, mounting said robot on said attachment member;
   correlating said at least two intraoperative images to form a pseudo three dimensional image, including said image referencing element;
   selecting a first window from said pseudo three dimensional image, said first window being selected from the region of said attachment member to include features associated with said bone, and registering said first window with a second window in a similarly selected position from said initial three dimensional image, whereby to form a window registration;
   utilizing said window registration to correlate said pseudo three dimensional image with said initial three dimensional image such that the location of said image referencing element is determined with respect to said initial three dimensional image; and
   utilizing said surgical robot to perform said surgical procedure in accordance with said surgical plan.

2. A method according to claim 1, wherein said image referencing element comprises at least three reference markers having known mutual positions.

3. A method according to claim 1, wherein said image referencing element which is included in said pseudo three dimensional image is utilized to correlate the position of said attachment member to said bone.

4. A method according to claim 1, wherein said initial three dimensional image comprises at least one of a magnetic resonance image, a Computerized Tomography image, an ultrasound image or an image extracted from a CAD model.

5. A method according to claim 1, wherein said at least two intraoperative images of the surgical site comprise at least two C-arm X-ray images.

6. A method according to claim 5, wherein said at least two C-arm images are taken at angles substantially spaced from each other.

7. A method according to claim 1, further comprising:
   prior to forming said pseudo three dimensional image of the surgical site, calibrating said at least two intraoperative images using said image reference element.

8. A method according to claim 1, further comprising:
   prior to generating said pseudo three dimensional image of the surgical site, calibrating said at least two intraoperative images using known reference dimensions associated with said attachment member.

9. A method according to claim 1, wherein said correlating the pseudo three dimensional image with the initial three dimensional image comprises registering additional windows of said initial three dimensional image with additional windows of said pseudo three dimensional image.

10. A method according to claim 1, further comprising:
    providing a surgical tool for said surgical robot; and
    using said robot to position said surgical tool according to the surgical plan.

11. A method according to claim 10, wherein said surgical tool includes a guide sleeve, and said method further comprises inserting said tool through said guide sleeve to said surgical site.

12. A method according to claim 1, wherein said registering said windows is based on either matching of geometric features in said first window of said pseudo three dimensional image with geometric features in said second window, or on matching of intensity features in said first window of said pseudo three dimensional image with intensity features in said second window.

13. A method according to claim 12, wherein said geometric features are any one of anatomical landmarks, implanted fiducials or contour points.

14. A method according to claim 1, wherein said attachment member is operative as a base for mounting said image referencing element, and thereafter, as a base for mounting said robot.

15. A method for performing a surgical procedure at a surgical site, comprising:
    utilizing an initial three dimensional image of said surgical site to provide a surgical plan of said procedure;
    attaching a surgical robot to a bone associated with the surgical site, said robot having at least one of (a) known dimensions or (b) markers attached to it in predetermined locations;
    generating at least two intraoperative images of said surgical site, which intraoperative images include at least one of (a) said known dimensions of said robot or (b) said markers attached in predetermined locations to said robot;
    correlating said at least two intraoperative images to form a pseudo three dimensional image, which pseudo three dimensional image includes at least one of (a) said known dimensions of said robot or (b) said markers;
    selecting a first window from said pseudo three dimensional image, said first window being selected to include features associated with said bone, and registering said first window with a second window in a similarly selected position from said initial three dimensional image, whereby to form a window registration;
    utilizing said window registration to correlate said pseudo three dimensional image with said initial three dimensional image such that the location of said robot is determined with respect to said initial three dimensional image; and utilizing said surgical robot to perform said surgical procedure in accordance with said surgical plan.

16. A method according to claim 15, wherein said inclusion of at least one of (a) said known dimensions of said robot or (b) said markers attached in predetermined locations to said robot in said pseudo three dimensional image is utilized to correlate the position of said robot to said bone.

17. A method according to claim 15, wherein said correlating the pseudo three dimensional image with the initial three dimensional image comprises registering additional windows of said initial three dimensional image with additional windows of said pseudo three dimensional image.

18. A method according to claim 15, further comprising:
providing a surgical tool for said surgical robot; and
using said robot to position said surgical tool according to the surgical plan.

19. A method according to claim 15, wherein said window registration is based either on matching of geometric features in said first window of said pseudo three dimensional image with geometric features in said second window in a similarly selected position from said initial three dimensional image, or on matching of intensity features in said first window of said pseudo three dimensional image with intensity features in said second window in a similarly selected position from said initial three dimensional image.

20. A method according to claim 19, wherein said geometric features are any one of anatomical landmarks, implanted fiducials or contour points.

21. A system for performing a surgical procedure at a surgical site, comprising:
a surgical robot for manipulating a tool to said surgical site;
an attachment member configured and dimensioned to attach the surgical robot to a bone associated with said surgical site;
an image referencing element adapted to be attached to said attachment member, such that the position of said attachment member is known relative to said image referencing element; and
a controller programmed to direct the robot to position the surgical tool at the surgical site,
wherein said controller is adapted to enable the system to perform the following steps of:
utilizing an initial three dimensional image of said surgical site to provide a surgical plan of said procedure;
correlating at least two intraoperative images of said surgical site, said images including said image referencing element but not including said surgical robot, to form a pseudo three dimensional image including said image referencing element;
selecting a first window from said pseudo three dimensional image, said first window being selected from the region of said attachment member to include features associated with said bone, and registering said first window with a second window from a similarly selected position from said initial three dimensional image to form a window registration; and
utilizing said window registration to correlate said pseudo three dimensional image with said initial three dimensional image such that the location of said image referencing element is determined with respect to said initial three dimensional image.

22. A system according to claim 21, wherein said initial three dimensional image comprises at least one of a magnetic resonance image, a Computerized Tomography image, an ultrasound image or an image extracted from a CAD model.

23. A system according to claim 21, wherein said intraoperative images of the surgical site comprise C-arm X-ray images.

24. A system according to claim 21, wherein said correlating the pseudo three dimensional image with the initial three dimensional image comprises registering additional windows of said initial three dimensional image with additional windows of said pseudo three dimensional image.

25. A system according to claim 21, wherein said window registration is based on either matching of geometric features in said first window with geometric features in said second window, or matching of intensity features in said first window with intensity features in said second window.

26. A system for performing a surgical procedure at a surgical site, comprising:
a surgical robot for manipulating a tool to said surgical site, said robot having at least one of (a) known dimensions or (b) markers attached to it in predetermined locations;
an attachment member configured and dimensioned to attach the surgical robot to a bone associated with said surgical site; and
a controller programmed to direct the robot to position the surgical tool at the surgical site,
wherein said controller is adapted to direct the system to perform the following steps of:
utilizing an initial three dimensional image of said surgical site to provide a surgical plan of said procedure;
correlating at least two intraoperative images of said surgical site including at least one of (a) said known dimensions of said robot or (b) said markers attached in predetermined locations to said robot, to form a pseudo three dimensional image including at least one of (a) said known dimensions of said robot or (b) said markers;
selecting a first window from said pseudo three dimensional image, said first window being selected from the region of said attachment member to include features associated with said bone, and registering said first window with a second window from a similarly selected position from said initial three dimensional image to form a window registration; and
utilizing said window registration to correlate said pseudo three dimensional image with said initial three dimensional image such that the location of said robot is determined with respect to said initial three dimensional image.

27. A system according to claim 26, wherein said initial three dimensional image comprises at least one of a magnetic resonance image, a Computerized Tomography image, an ultrasound image or an image extracted from a CAD model.

28. A system according to claim 26, wherein said intraoperative images of the surgical site comprise C-arm X-ray images.

29. A system according to claim 26, wherein said correlating the pseudo three dimensional image with the initial three dimensional image comprises registering additional windows of said initial three dimensional image with additional windows of said pseudo three dimensional image.

30. A system according to claim 26, wherein said window registration is based either on matching of geometric features in said first window with geometric features in said second window, or on matching of intensity features in said first window with intensity features in said second window.

* * * * *